United States Patent
Shibusawa et al.

(10) Patent No.: US 6,900,346 B2
(45) Date of Patent: May 31, 2005

(54) METHOD FOR DECOMPOSITION OF MICHAEL TYPE ADDUCT

(75) Inventors: Fumio Shibusawa, Hyogo (JP); Naoki Serata, Himeji (JP); Kazuhiko Sakamoto, Himeji (JP)

(73) Assignee: Nippon Shokubai Co., Inc., Osaka (JP)

( * ) Notice: Subject to any disclaimer, the term of this patent is extended or adjusted under 35 U.S.C. 154(b) by 217 days.

(21) Appl. No.: 10/183,840

(22) Filed: Jun. 27, 2002

(65) Prior Publication Data

US 2003/0028051 A1 Feb. 6, 2003

(30) Foreign Application Priority Data

Jul. 10, 2001 (JP) ........................................ 2001-209080
Apr. 25, 2002 (JP) ........................................ 2002-124302

(51) Int. Cl.[7] ........................ C07C 69/52; C07C 51/42
(52) U.S. Cl. ........................................ 560/205; 562/600
(58) Field of Search ........................... 560/205; 562/600

(56) References Cited

U.S. PATENT DOCUMENTS

| 3,487,101 A | 12/1969 | Volker et al. |
| 3,868,410 A | 2/1975 | Horlenko et al. |
| 5,877,344 A * | 3/1999 | Gande et al. |
| 6,498,272 B1 | 12/2002 | Schroder et al. |
| 6,512,138 B1 * | 1/2003 | Dams et al. |

FOREIGN PATENT DOCUMENTS

| EP | 0765856 A1 | 4/1997 |
| EP | 0781759 A2 | 7/1997 |
| JP | B-45-19281 | 7/1970 |
| JP | A-49-55614 | 5/1974 |
| JP | A-3-178949 | 9/1990 |
| WO | WO 00/53560 | 9/2000 |

* cited by examiner

Primary Examiner—Johann Richter
Assistant Examiner—Paul A. Zucker
(74) Attorney, Agent, or Firm—Mathews, Collins, Shepherd & McKay, P.A.

(57) ABSTRACT

A method for the decomposition of a Michael type adduct, characterized by causing a Michael type adduct to react in the presence of an N-oxyl compound thereby decomposing the Michael type adduct into acrylic acid and/or the acrylic ester and/or the alcohol and a method for the production of acrylic acid and/or the acrylic ester, characterized by comprising a step of recovering a Michael type adduct formed in the process for the production of acrylic acid or acrylic ester and a step of decomposing the recovered Michael type adduct by the method of decomposition mentioned above. This invention, therefore, allows promotion of efficient utilization of the raw materials.

4 Claims, 2 Drawing Sheets

METHOD FOR DECOMPOSITION OF MICHAEL TYPE ADDUCT

BACKGROUND OF THE INVENTION

1. Field of the Invention

This invention relates to a method for the decomposition of a Michael type adduct of acrylic acid and/or an acrylic ester and more particularly to a method for the decomposition of a Michael type adduct, characterized by decomposing a Michael type adduct by-produced during the production of acrylic acid or an ester thereof by the action of heat or a catalyst, for example, in the presence of an N-oxyl compound into acrylic acid and/or an acrylic ester and/or at least one species of alcohol.

2. Description of the Related Art

Generally, during the production of acrylic acid and an ester thereof, a Michael type adduct having a carboxylic acid and an alcohol added to the carbon-carbon double bond of the acrylic acid and the acrylic ester is possibly by-produced by the action of heat or a catalyst, for example. Such Michael type adducts include about dimers to pentamers of acrylic acid, esters thereof, alkoxypropionic acids, and alkoxypropionic esters, for example.

When the quantity of the by-produced Michael type adduct increases, this increase brings the disadvantage of degrading the efficiency of raw materials in the process for the production of acrylic acid and an acrylic ester and boosting the cost of production. Further, when the Michael type adduct is suffered to accumulate in the process, it greatly hinders the step of purification and the step of production and, owing to the elevation of temperature and the formation of a by-product which ensues, possibly degrades the quality of a product. Thus, the Michael type adduct is generally concentrated at the step of purification, expelled from the process, and incinerated in the ambient air. This incineration is unfavorable from the viewpoint of the preservation of the environment. At the plant for the production of acrylic acid, therefore, efforts have been directed toward decomposing the Michael type adduct and reclaiming the products of the decomposition.

In regards to a method for decomposing such a Michael type adduct, it has been heretofore known that the oligomers of acrylic acid or an acrylic ester, alkoxypropionic acids, and alkoxypropionic esters are thermally decomposed or decomposed by the use of a catalyst. To be specific, JP-A-49-55614 discloses a method which consists in heating the Michael type adduct by-produced during the esterification of acrylic acid with an alcohol at a temperature of not lower than 180° C. thereby decomposing the adduct into monomers. Then, JP-B-45-19281 discloses a method which produces acrylic acid by heating the residue produced at the step for finishing acrylic acid in the presence of a catalyst such as a compound possessing a primary or tertiary amino group or a tertiary phosphine.

These methods, however, require fairly high temperatures and, in the meantime, suffer from unduly low recovery of acrylic acid. Further, an attempt to heighten the recovery in these methods results in promoting secondary reactions, copiously forming such by-products as high boiling substances and low boiling substances which degrade the quality of acrylic acid or an acrylic ester, and consequently rendering recovery of acrylic acid in high yields difficult.

Further, JP-A-03-178949 discloses a method for recovering monomers by catalytically decomposing the Michael type adduct by-produced during the production of acrylic acid and an ester thereof in the presence of a solid acid at an elevated temperature of not lower than 200° C. This method has a high decomposition of the Michael type adduct. Since the reaction of this method proceeds at a high temperature, however, it forms such by-products as light boiling substances at a high ratio and consequently brings an adverse effect on the quality of a product. Further, since the decomposition is a solid-liquid reaction, the catalytic activity is conspicuously degraded by poisoning. Moreover, since all the methods described above invariably resort to high-temperature reactions and consequently produce highly viscous residues, they are at a disadvantage in suffering the residues to solidify eventually after protracted stagnation and rendering the disposal of the solidified residues extremely difficult. Under these circumstances, the desirability of converting the Michael type adduct into at least one of such useful compounds as acrylic acid, esters thereof, and alcohols and efficiently recovering or utilizing the product of conversion has been finding enthusiastic recognition.

SUMMARY OF THE INVENTION

The present inventors, as a result of pursuing a study in search of a method for decomposing the Michael type adduct formed during the process for producing acrylic acid and esters thereof, have found that the presence of an N-oxyl compound under the conditions existing during the production of acrylic acid, for example, enables the Michael type adduct to be decomposed into useful components at a low temperature in a high yield while preventing the formation of such by-products as light boiling substances and the thickening and gelation of the reaction solution and that the product of this decomposition is acrylic acid, an ester thereof, or an alcohol corresponding to the ester. This invention has been perfected based on the knowledge. The activity so manifested by the N-oxyl compound in decomposing the Michael type adduct during the process for producing acrylic acid, for example, has never been known to the art.

According to this invention, when the Michael type adduct is left reacting in the presence of an N-oxyl compound, it is enabled to be decomposed into acrylic acid, an acrylic ester, and/or an alcohol. By incorporating this method of decomposition in the process for producing acrylic acid or an acrylic ester, it is made possible to improve the efficiency of utilization of raw materials and exalt the yield of production.

DESCRIPTION OF THE PREFERRED EMBODIMENTS

Figure 1:
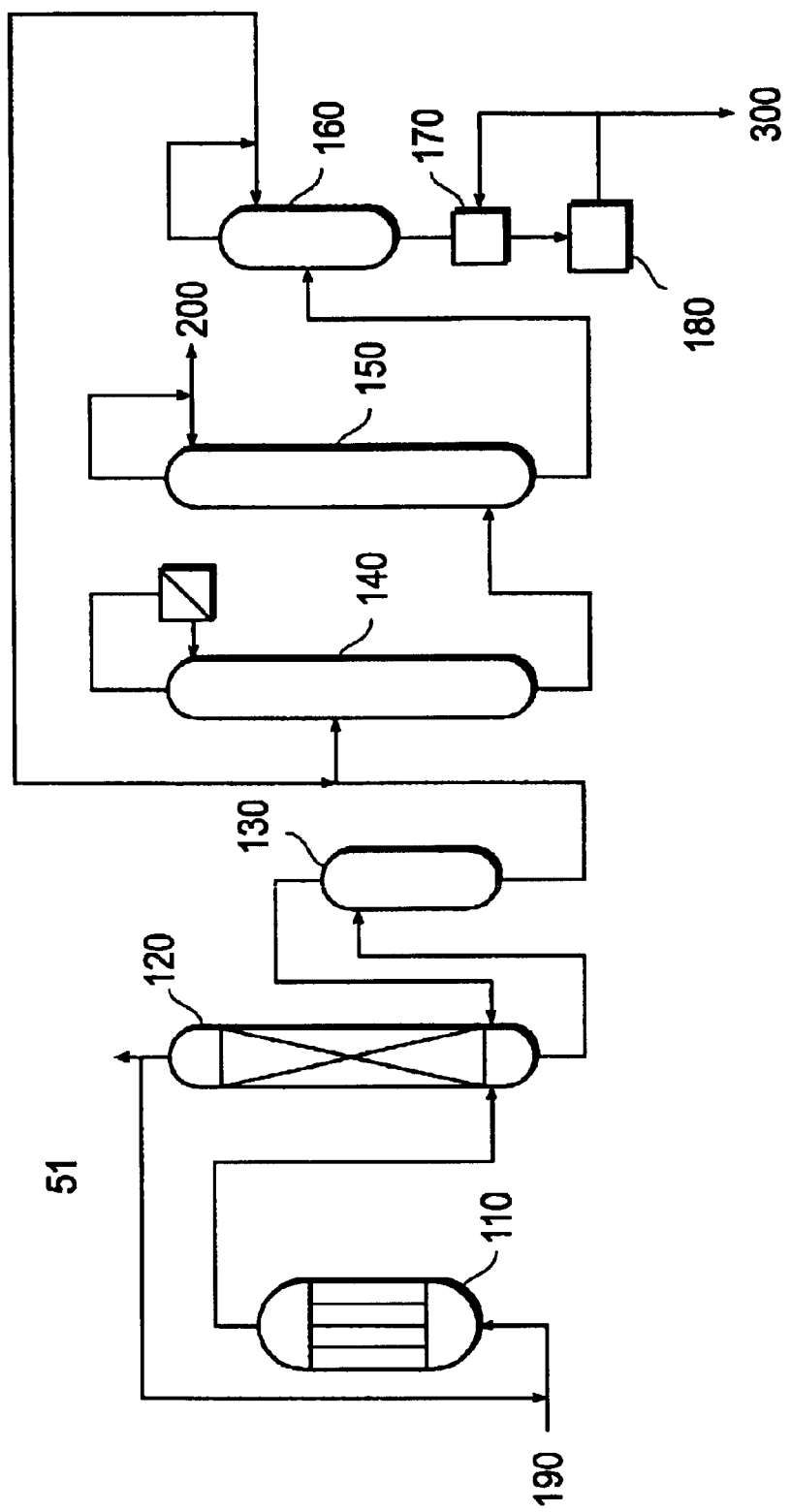
FIG. 1 is a schematic flow diagram illustrating a process for the production of acrylic acid.

This invention concerns a method for decomposing a Michael type adduct, characterized by allowing the Michael type adduct to react in the presence of an N-oxyl compound thereby decomposing it into an acrylic acid and/or an acrylic ester and/or an alcohol.

The Michael type adduct which forms the target for this invention is a Michael type adduct which is by-produced in the process for the production of acrylic acid or ester thereof.

It is a compound represented by the following formula [I] or the following formula [II][[·]]

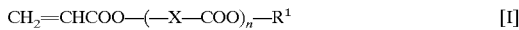

$$CH_2=CHCOO-(-X-COO)_n-R^1 \qquad [I]$$

(wherein n denotes an integer of 1–5, $R^1$ denotes a hydrogen atom or an alkyl group, and —X— denotes —$CH_2CH_2$— or —$CH(CH_3)$—, providing that the plurality of —X— may be identical or not identical when n is not less than 2[[·]])

$$R^2-O-(-X-COO)_m-R^3 \qquad [II]$$

(wherein m denotes an integer of 1–5, $R^2$ and $R^3$ independently denote a hydrogen atom or an alkyl group, and —X— denotes —$CH_2CH_2$— or —$CH(CH_3)$—, providing that the plurality of —X— may be identical or not identical when m is not less than 2[[·]]).

The alkyl groups denoted by $R^1$, $R^2$, and $R^3$ in Formulas [I], [II] originate in the alcohol used as the raw material for the production of an acrylic ester. As concrete examples of such alkyl groups, linear or branched alkyl groups, alkyl groups having an aromatic group substituted for the hydrogen atom of the alkyl group, and cyclo ring-containing alkyl groups having a cycloalkyl group substituted for the hydrogen atom of the alkyl group may be cited. The alkyl groups denoted by $R^1$, $R^2$, and $R^3$ include alkyl groups of 1–8 carbon atoms such as, for example, methyl group, ethyl group, n-butyl group, t-butyl group, propyl group, 2-ethylhexyl group, benzyl group having phenyl group linked to methyl group, and 2-cyclopentyl methyl group having cyclopentane linked to methyl group. For this invention, $R^1$, $R^2$, and $R^3$ are preferred to denote independently a hydrogen atom, methyl group, ethyl group, t-butyl group, or 2-ethylhexyl group. The reason for this preference is that the formulas represent such compounds as are by-produced in the process for the production of acrylic acid and/or ester thereof.

Then, —X— denotes —$CH_2CH_2$— or —$CH(CH_3)$— and n denotes an integer of 1–5, preferably 1–2. The reason for this choice of the integer is based on the face that that in the process for the production of acrylic acid and acrylic ester, their dimers and trimers are by-produced at high ratios. The symbol m in Formula [II] denotes an integer of 1–5, preferably 1–2. The reason for this choice of the integer is that in the process for the production of an acrylic ester, alkoxypropionic acids and esters thereof are by-produced at high ratios. Such Michael type adducts are by-produced in the process for the production of acrylic acid and acrylic esters. Since this invention can recover such a Michael type adduct efficiently as useful acrylic acid, namely at least one compound selected from among acrylic acid, acrylic esters, and alcohols, it allows a substantial improvement in the yield in the process for the production of acrylic acid and esters thereof.

This invention contemplates decomposing the Michael type adduct mentioned above in the presence of the N-oxyl compound. As the N-oxyl compound, any of popularly known N-oxyl compounds which possess such a catalytic activity as to decompose the Michael type adduct mentioned above and find extensive utility for the decomposition may be used. It is particularly advantageous to use, among other N-oxyl compounds, one or more compounds selected from the group consisting of 4,4',4"-tris-(2,2,6,6-tetramethylpiperidinoxyl) phosphite and 2,2,6,6-tetramethylpiperidinoxyls represented by the following formula (1):

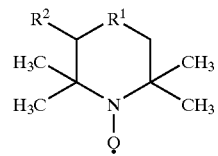

(1)

(wherein $R^1$ denotes $CH_2$, CHOH $CHCH_2OH$, $CHCH_2CH_2OH$, $CHOCH_2OH$, $CHOCH_2CH_2OH$, CHCOOH, or C=O and $R^2$ denotes a hydrogen atom or $CH_2OH$).

In this invention, one or more compounds selected from the group consisting of N-hydroxy-2,2,6,6-tetramethylpiperidine compounds such as, for example, 1,4-dihydroxy-2,2,6,6-tetramethylpiperidine and 1-hydroxy-2,2,6,6-tetramethylpiperidine and 2,2,6,6-tetramethylpiperidine compounds such as, for example, 2,2,6,6-tetramethylpiperidine and 4-hydroxy-2,2,6,6-tetramethylpiperidine may be used in combination of the N-oxyl compound. Incidentally, N-hydroxy-2,2,6,6-tetramethylpiperidine compounds and 2,2,6,6-tetramethylpiperidine compounds are possibly contained as impurities in the commercially available N-oxyl compound products. In this case, the use of such a commercially available N-oxyl compound constitutes the additional use of an N-hydroxy-2,2,6,6-tetramethylpiperidine compound or a 2,2,6,6-tetramethylpiperidine compound in combination with an N-oxyl compound.

This invention is characterized by decomposing the Michael type adduct in the presence of the N-oxyl compound into acrylic acid and/or acrylic ester and/or alcohol. It particularly brings the advantage that the alcohol formed by the decomposition does not easily form such by-products as alkenes and ethers by an intramolecular dehydrating reaction or intermolecular dehydrating reaction.

The quantity of the N-oxyl compound to be properly used from the viewpoint of the efficiency and cost of conversion is in the range of 0.01–20% by weight, preferably in the range of 0.1–10% by weight, and particularly preferably in the range of 1–6% by weight, based on the total quantity of the Michael type adduct represented by Formula [I] or [II]. In this case, the method for adding the N-oxyl compound does not need to be particularly restricted. This compound may be supplied in a solidified state or in a gasified state to the decomposition tank besides being supplied as dissolved in a solvent. Otherwise, it may be supplied directly to the decomposition tank or added at any of the preceding steps. As a way of allowing the compound to fulfill its function in a dissolved state, for example, the method of dissolving the N-oxyl compound in a proper solvent and supplying the resultant solution to the prospective site of reaction may be cited. Then, as a way of allowing the compound to fulfill its function in a, gasified state, the method of gasifying or subliming the N-oxyl compound and supplying the product of gasification or sublimation into the path communicating with the decomposition tank so as to be mixed with the rest of the reactants. The solvents which are capable of dissolving the N-oxyl compound mentioned above include acrylic acid, acrylic esters, alcohols, water, benzene, toluene, xylene, cyclohexane, acetone, methylethyl ketone, methylisobutyl ketone, n-hexane, heptane, and mixtures thereof, for example.

This invention may optionally perform the reaction thereof by using additionally an alkali metal salt compound and/or an alkaline earth metal salt compound in combination with the N-oxyl compound mentioned above. This combined use improves both the conversion and the selectivity coefficient of the dimer of acrylic acid. The alkali metal salt compounds include salt compounds of lithium, sodium, potassium, rubidium, cesium, and francium, for example. It is preferable to use salt compounds of lithium, sodium, and potassium because they possess an excellent ability to decompose the Michael type adduct of acrylic acid. As concrete examples of such salt compounds, acrylates such as sodium acrylate, potassium acrylate, and lithium acrylate; hydroxides such as sodium hydroxide, potassium hydroxide, and lithium hydroxide; hydrides such as sodium hydrogen hydride and sodium hydride; halogenides such as sodium fluoride, sodium chloride, sodium bromide, and sodium iodide; oxygen compounds such as sodium peroxide and sodium superoxide; sulfides such as sodium sulfide; nitrogen compounds such as sodium amide and sodium azide; oxacides such as sodium hypochlorite; alkoxides represented by RONa wherein R denotes an alkyl group of 1–5 carbon atoms; and sulfates, nitrates, phosphates, carbonates, silicates, oxalates, and acetates of alkali metals may be cited. These salt compounds may be used either singly or in the form of a combination of two or more members.

Then, the alkaline earth metal salt compounds include salt compounds of beryllium, magnesium, calcium, strontium, barium, and radium, for example. It is preferable to use the salt compounds of magnesium, calcium, and barium because they possess an excellent ability to decompose the Michael type adduct of acrylic acid. As concrete examples of such salt compounds, acrylates such as calcium acrylate, magnesium acrylate, and barium acrylate; hydroxides such as calcium hydroxide, magnesium hydroxide, and barium hydroxide; hydrides such as calcium hydride; chlorides such as calcium fluoride and calcium chloride; and sulfates, nitrates, phosphates, carbonates, silicates, oxalates, and acetates of alkaline earth metals may be cited. These salt compounds may be used either singly or in the form of a combination of two or more members. In this invention, it is preferable to use acrylates of alkali metals or alkaline earth metals. The reason for the preference of such acrylates is that the acrylic acid resulting from ionic dissociation can be used as a target compound for the production.

The total quantity of the alkali metal salt compound and/or the alkaline earth metal salt compound to be used is in the range of 0.01–10% by weight, preferably in the range of 0.05–5% by weight, and particularly preferably in the range of 0.1–2% by weight, based on the total quantity of the Michael type adduct represented by Formula [I] or [II]. If the quantity falls short of 0.01% by weight, the shortage will degrade the efficiency of the reaction and prevent the conversion into an acrylic acid to be attained with fully satisfactory efficiency. Conversely, if this quantity exceeds 10% by weight, the excess will possibly induce formation of a residue of high viscosity and give rise to a commercially unfavorable situation.

The method for adding the alkali metal salt compound and/or the alkaline earth metal salt compound does not need to be particularly restricted. One or more compounds containing the alkali metal salt compound and/or the alkaline earth metal salt compound may be additionally used and added directly in a solidified state to the waste liquor containing the Michael type adduct of acrylic acid or acrylic acid dimer or may be supplied as dissolved in a solvent. It does not need to be added simultaneously with the N-oxyl compound.

As regards the site of introduction of the compound, the compound may be directly supplied to the decomposition tank for the Michael type adduct of acrylic acid. The supply is only required to enable the alkali metal salt compound and/or the alkaline earth metal salt compound to be ultimately contained with the Michael type adduct. Thus, the alkali metal salt compound and/or the alkaline earth metal salt compound or a solution thereof in a solvent may be introduced via a pipe serving the function of circulating a fluid to the decomposition tank. As a way of enabling such a salt compound to fulfill its function in the state of a solution, for example, the method of dissolving the alkali metal salt compound and/or the alkaline earth metal salt compound in a proper solvent and supplying the resultant solution may be cited. The solution may be supplied in a sprayed form. The solvents which can dissolve the aforementioned compound containing the alkali metal salt compound and/or the alkaline earth metal salt compound include acrylic acid, acrylic esters, alcohols such as methanol and ethanol, water, benzene toluene, acetone, methylethyl ketone, methylisobutyl ketone, and mixtures thereof, for example.

The temperature at which the Michael type adduct is made to react in the presence of the N-oxyl compound or under the additional use of the alkali metal salt compound and/or the alkaline earth metal salt compound is generally in the range of 100–250° C., preferably in the range of 120–200° C., and particularly preferably in the range of 130–180° C., though variable with the kind of oligomer as the target compound and the magnitude of reaction pressure. If this temperature exceeds 250° C., the excess will possibly aggravate side reactions unusually, lower the yield, increase such impurities as light boiling substances, and degrade the quality of a product. Further, the consequent stagnation of heat at elevated temperature will possibly induce formation of a residue of high viscosity and will possibly give rise to a commercially unfavorable situation of suffering the reactants to solidify within the vessel. While the decomposition has been heretofore required to proceed at a temperature of not lower than 180° C., this invention enables the decomposition into useful components to be effected efficiently at a lower temperature and, therefore, excels in thermal efficiency. If the temperature conversely falls short of 100° C., the shortage will possibly lower the reaction velocity and consequently degrade the efficiency of reaction and will possibly prevent the conversion into an acrylic acid as the target of production from proceeding with fully satisfactory efficiency. Incidentally, the pressure during the course of the reaction does not need to be particularly restricted. It is properly in the range of 0.01–1000 kPa(abs), preferably in the range of 0.1–500 kPa(abs), and particularly preferably in the range of 1–200 kPa(abs).

In this invention, it is preferable to use a polymerization inhibitor for the purpose of preventing the polymerization of acrylic acid, an acrylic ester, or an alcohol which is formed when the Michael type adduct is decomposed in the presence of the N-oxyl compound or under the additional use of the alkali metal salt compound and/or the alkaline earth metal salt compound. The polymerization inhibitor to be used may be any of the polymerization inhibitors which are generally used widely in the process for the production of acrylic acid. As concrete examples of the polymerization inhibitor, hydroquinone, methoxy hydroquinone, phenothiazine, and hydroxy amine may be cited. When the reaction of decomposition is carried out in the presence of a molecular oxygen, the effect of inhibiting polymerization can be exalted. Though the quantity of the polymerization inhibitor to be used does not need to be particularly restricted, the total quantity of the polymerization inhibitor so used is preferred to be in the range of 0.01–15% (based on weight) based on the quantity of the vapor of acrylic acid or an ester thereof.

The decomposition contemplated by this invention may be carried out by a batch method, a semicontinuous method, or a continuous method. The term "continuous method" as used herein means the mode in which the recovery of the Michael type adduct is continuously performed in the presence of the N-oxyl compound or the alkali metal salt compound and/or the alkaline earth metal salt compound and the Michael type adduct is decomposed. In this continuous method, the speed of supply of the Michael type adduct and the speed of decomposition thereof are preferred to be balanced. For the purpose of securing this balance, the method of reaction distillation is available. The time of retention in the decomposition tank used in the continuous method is generally in the range of 0.1–60 hours, preferably in the range of 5–50 hours, and particularly preferably in the range of 20–30 hours. If the retention time exceeds 60 hours, the excess will heighten the proportion of by-product and deteriorate the performance of a product and, when the decomposition tank is enlarged by way of compensation, will render the decomposition disadvantageous in terms of the cost of equipment. Conversely, if the retention time falls short of 0.1 hour, the shortage will possibly prevent the decomposition from proceeding fully satisfactorily.

The Michael type adduct is the component by-produced in the process for the production of acrylic acid and/or acrylic ester. The product of the decomposition of this Michael type adduct is the raw material compound for acrylic acid and/or acrylic ester or the object of production itself. By incorporating the method of decomposition contemplated by this invention in the process for the production of acrylic acid and/or acrylic ester, therefore, it is made possible to produce acrylic acid and/or acrylic ester excelling in quality with excellent operational efficiency. To be specific, the second aspect of this invention is directed toward a method for producing acrylic acid and/or acrylic ester, characterized by comprising a step of recovering a Michael type adduct of acrylic acid and/or acrylic ester by-produced during the process for the production of acrylic acid or acrylic ester and a step of decomposing the recovered Michael type adduct by the method of decomposition contemplated by the first aspect of this invention and optionally embracing further, subsequently to the step of decomposing the Michael type adduct, a step of returning at least one compound selected from the group consisting of acrylic acid, an acrylic ester, and an alcohol obtained by the decomposition of the Michael type adduct to the production of acrylic acid or the production of an acrylic ester. By additionally incorporating the step of provisionally recovering the Michael type adduct outside the system as described above, it is made possible to remove the by-product which is detrimental to the process for the production of acrylic acid or an acrylic ester and prevent the by-product from inducing temperature elevation of temperature during the process of the production and from deteriorating the quality of a product. By returning the product of decomposition obtained as described above to the system in the process for the production of acrylic acid or an acrylic ester, it is made possible to exalt the efficiency of raw material.

As one example of the method for producing acrylic acid by embracing the step of recovering the Michael type adduct and the step of decomposing the recovered Michael type adduct, the method which comprises subjecting propylene and/or acrolein to gas-phase catalytic oxidation thereby obtaining an acrylic acid-containing gas and subsequently refining the gas will be described below with reference to FIG. 1. Incidentally, since the Michael type adduct has a higher boiling point than acrylic acid, it is recovered in the high boiling substance-containing fraction in the process for the production of acrylic acid.

First, propylene (190) and a molecular oxygen-containing gas are supplied to a catalytic gas phase reactor (110) provided with an intermediate tube sheet partitioning the reactor into an upper and a lower chamber and subjected to catalytic gas phase oxidation to obtain an acrylic acid-containing gas. This reaction gas is introduced into an acrylic acid absorption column (120) and brought into contact with water to collect the acrylic acid in an aqueous solution. Since this acrylic acid-containing solution contains acrolein as an impurity, it is introduced into an acrolein dissipating column (130) and made to dissipate acrolein therein to obtain an aqueous acrylic acid solution containing 30% by weight of water and 3.0% by weight of acetic acid. Then, the bottom liquid of the acrolein dissipating column (130) is introduced into an azeotropic dehydrating column (140) and an azeotropic solvent is supplied thereto and they are together distilled to expel part of the water and the acrylic--acid through the top of the azeotropic dehydrating column (140). Consequently, a bottom liquid containing 97.5% by weight of acrylic acid, 0.03% by weight of acetic acid, 0.02% by weight of water, and 2.45% by weight of other components is obtained. Then, this bottom liquid is introduced into a rectifying column (150) to obtain acrylic acid (200) as a finished product through the top of the column. The bottom liquid of the rectifying column (150) is a liquid containing Michael type adducts of acrylic acid dimer, for example, namely acrylic acid dimer, acrylic acid trimer, acrylic acid, maleic acid, and stabilizer, and high-boiling substances.

In this invention, the bottom liquid containing the Michael type adduct is introduced into the intermediate stage of a high boiling separating column (160) provided with a thin-film distilling device (170). While the bottom temperature of the high boiling separating column (160) is controlled by the operating temperature of the thin-film distilling device (170), the Michael type adduct-containing bottom liquid of the thin-film distilling device (170) is introduced into a thermally decomposition tank (180). To the thermally decomposition tank (180), the N-oxyl compound (4-hydroxy-2,2,6,6-tetramethylpiperidinoxyl) is added in such a quantity as to account for 2% by weight based on the waste liquid (300) obtained from the decomposition tank (180). The temperature of the interior of the decomposition tank is preferred to be in the range of 120–150° C. The decomposition tank (180) may be furnished with a heat source, though omitted from illustration in the diagram, for the purpose of insulating or heating the tank. Since the decomposition liquid contains acrylic acid and other components, part of this liquid is circulated to the thin-film distilling device (170) to expel acrylic acid by distillation through the top of the high-boiling separating column (160) and circulate it to the azeotropic dehydrating column (140). Incidentally, part of the decomposition liquid is withdrawn as the waste liquid (300) out of the system.

Figure 2:
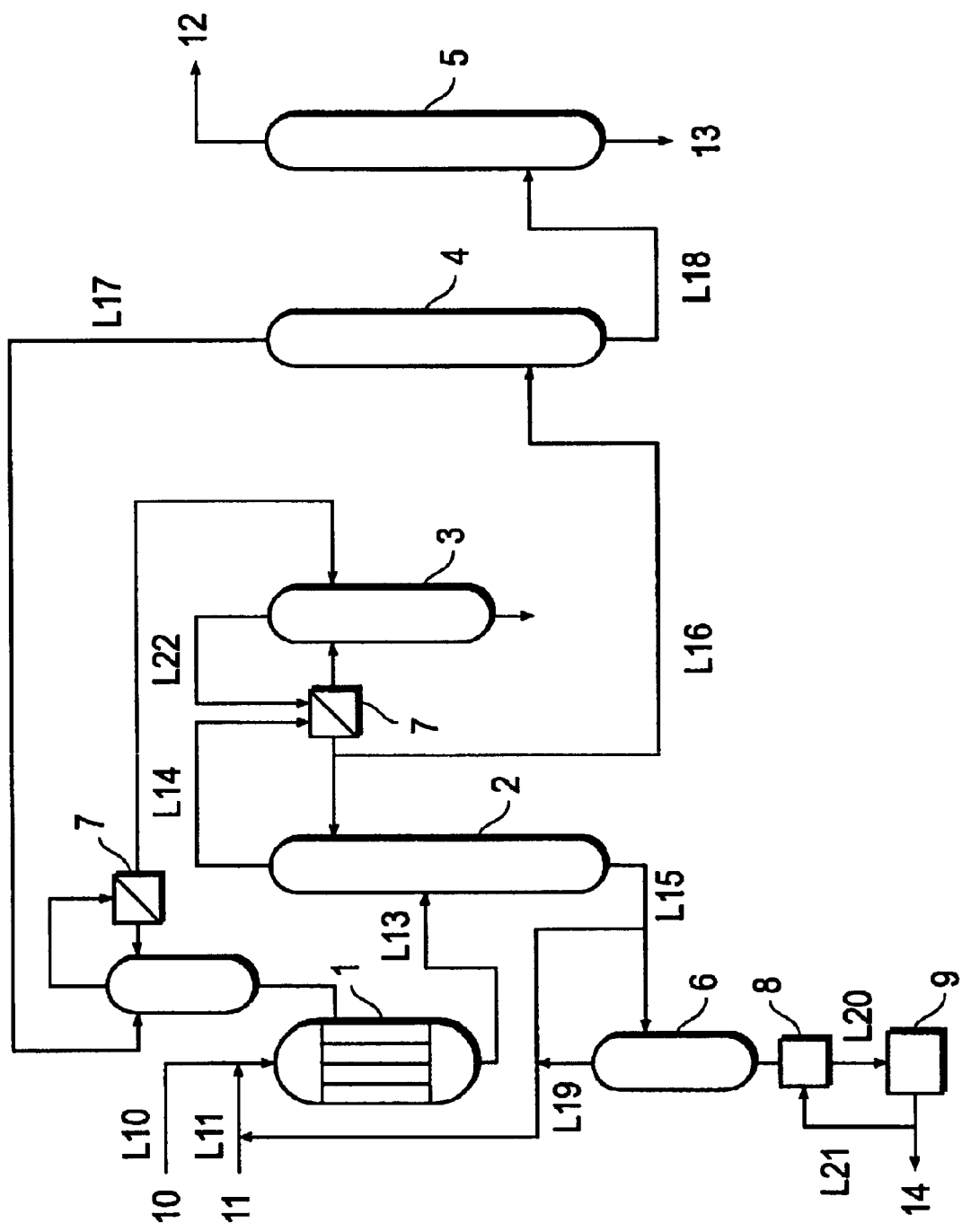
FIG. 2 is a schematic diagram illustrating the process for producing an acrylic ester.

As one example of the method for producing acrylic ester, the method for producing acrylic ester by preparing acrylic acid by catalytic gas phase oxidation and then esterifying the acrylic acid will be specifically described below with reference to FIG. 2.

To an esterification reactor (1) packed with a strongly acidic cation resin as a catalyst, acrylic acid (11) is supplied via a line (L11) and alcohol (10) is supplied via a line (L10)

to get an ester through the catalyst. The interior of the esterification reactor (1) contains acrylic acid as the raw material for the production of the acrylic ester, alcohol, and an acrylic ester as the product of reaction. Then, the reaction solution is introduced into an acid separating column (2) via a line (L13) and the bottom liquid containing high-boiling substances is introduced into a high-boiling separating column (6) to induce expulsion of such light-boiling substances as an acrylic ester, unaltered alcohol, and water through the top of the column by distillation. When the distillate is introduced into an oil-water separating device (7), it is separated into an oil phase containing the acrylic ester and a water phase formed mainly of water and alcohol. Thus, the water phase is transferred to an alcohol recovering column (3) and the oil phase is supplied to a light-boiling separating column (4) via a line (L16). At this time, part of the oil phase may be refluxed to the acid separating column (2). In the meantime, the acrylic ester is extracted from the light-boiling separating column (4) via the bottom and supplied to a rectifying column (5) via a line (L18). The acrylic ester as a finished product (12) is expelled by distillation through the column top. The alcohol which is expelled by distillation through the top of an alcohol recovering column (3) is circulated to the oil phase in the oil-water separating device (7) via a line (L22). The light-boiling substances such as water, alcohol and other components which are expelled by distillation from the light-boiling separating column (4) through the top thereof may be circulated to the esterification reactor (1) via a distilling column disposed on the esterification reactor (1).

The bottom liquid of the acid separating column (2) which is introduced into the high-boiling separating column (6) in the process for producing the acrylic ester in the manner described above contains such Michael type adducts as acrylic acid dimer and esters thereof, alkoxypropionic acid, and alkoxypropionic esters in conjunction with such raw material components as acrylic acid. Thus, the bottom liquid containing such Michael type adducts is introduced into the high-boiling separating column (6) provided with a thin-film distilling column (8) to expel and recover acrylic acid through the top of the column and, at the same time, the bottom liquid of the column containing the Michael type adducts is introduced into the thin-film distilling device (8) and subjected to a treatment for further distillation to obtain a bottom liquid. When the bottoms is introduced into a thermal decomposition tank (9) via a line (L20), made to add the N-oxyl compound thereto, and then heated, the Michael type adducts are decomposed into such raw material components as acrylic acid and alcohol and acrylic esters. When the product of this decomposition is introduced into the thin-film distilling device (8), alcohol, acrylic acid, and acrylic esters are advanced through the high-boiling separating column (6) and expelled by distillation through the top of the column. They are circulated via a line (L19) and the line (L11) to the esterification reactor (1). The return of the mixture of the products of decomposition to the step of esterification or acid separation proves particularly advantageous because the other components can be separated at and after the subsequent step. Optionally, these components may be separated for reuse by such methods as distillation and extraction.

The expression "a step of recovering the Michael type adduct" as used in the present specification refers to the step for obtaining a fraction containing the Michael type adduct, which step is only required to be capable of decomposing the Michael type adducts subsequently contained in the fraction into acrylic acid and/or an acrylic ester in the presence of the N-oxyl compound. It extensively embraces steps for introducing the fraction containing the Michael type adducts into the decomposition tank, for example.

Incidentally, the production of acrylic ester is attained by a method which consists in subjecting acrylic acid and alcohol to a reaction of dehydration and consequently obtaining a corresponding ester. As concrete examples of the alcohol which is advantageously used herein, methanol, ethanol, n-butanol, isobutanol, sec-butanol, t-butanol, 1-pentanol, 2-pentanol, 3-pentanol, cyclopentanol, 1-hexanol, 2-hexanol, 3-hexanol, cyclohexanol, 1-heptanol, 2-heptanol, 3-heptanol, 1-octanol, isooctanol, 3-ethylhexanol, isononyl alcohol, and lauryl alcohol may be cited. They may be in a linear form or a branched form. These alcohols may be used either singly or in the form of a combination of two or more members.

This invention concerns a method for decomposing the Michael type adduct by using the N-oxyl compound. Since the Michael type adduct is formed during the process for the production of acrylic acid or ester thereof as described above, the method of decomposition contemplated by this invention is enabled by adding the N-oxyl compound to the process of the production mentioned above to produce acrylic acid and an ester thereof while it decomposes the Michael type adduct.

Incidentally, the Michael type adduct which forms the subject for the decomposition contemplated by this invention does not need to be limited to the Michael type adduct by-produced during the process for the production of acrylic acid and ester thereof. The Michael type adduct, therefore, may be caused to react in the presence of the N-oxyl compound batch wise and consequently decomposed into acrylic acid and/or acrylic ester and/or an alcohol. Without reference to the kind of method, the decomposition can be accomplished at the reaction temperature under the reaction pressure mentioned above.

Embodiments

Now, this invention will be described more specifically below with reference to working examples thereof.

EXAMPLE 1

A Michael type adduct was decomposed by a batch reaction. For a start, in a round flask having an inner volume of 500 ml and provided with a condenser tube, 15 g of 4H-TEMPO (4-hydroxy-2,2,6,6-tetramethylpiperidinoxyl) as a catalyst and 300 g of a Michael type adduct (composed of 60% by weight of acrylic acid dimer (hereinafter abbreviated as "DAA"), 4% by weight of acrylic acid, 2% by weight of hydroquinone, and 34% by weight of other high-boiling impurities) were placed and stirred at a temperature of 140° C. till they reacted.

Four hours after the start of the reaction, the decomposition liquid was analyzed by gas chromatography. The results were shown in Table 1. The conversion and the selectivity coefficient indicated in Table 1 were calculated by the following formulas.

Conversion, %

=[(Quantity of Michael type adduct decomposed)/(quantity of Michael type adduct prior to the decomposition)]×100

Selectivity coefficient, %

=[(Total quantity of acrylic acid, acrylic ester, and alcohol formed)/(quantity of Michael type adduct prior to the decomposition)]×100

EXAMPLE 2

The decomposition of a Michael type adduct was carried out by following the procedure of Example 1 while changing the quantity of 4-TEMPO to 14.9 g and additionally using 0.1 g of 1,4-dihydroxy-2,2,6,6-tetramethylpiperidine. The results were shown in Table 1.

EXAMPLE 3

The decomposition of a Michael type adduct was performed by a batch reaction by following the procedure of Example 1 while further adding 3 g of sodium hydroxide (NaOH) as a catalyst. The results were shown in Table 1. The composition of the Michael type adduct was identical with that used in Example 1.

EXAMPLE 4

A Michael type adduct was decomposed by cracking distillation. For a start, a decomposition tank (1000 ml flask) having a 20-step distilling column disposed thereon and provided with a stirrer was charged with 500 g of a Michael type adduct (composed of 60% by weight of DAA, 4% by weight of acrylic acid, 2% by weight of hydroquinone, and 34% by weight of other high-boiling impurities). With the decomposition tank controlled to an operating pressure of 35 hPa and a column temperature of 140° C., the Michael type adduct was continuously introduced at a rate of 245 g/h and the 4H-TEMPO at a rate of 5 g/h. At the same time, acrylic acid and an acrylic ester formed by the decomposition were expelled by distillation from the distilling column through the top thereof. When the reflux ratio of the two compounds reached 1, the distillate and the liquid extracted from the decomposition tank were analyzed by gas chromatography. The results were shown in Table 1.

EXAMPLE 5

In a round flask provided with a condenser tube and having an inner volume of 500 ml, 15 g of 4H-TEMPO (4-hydroxy-2,2,6,6-tetramethylpiperidinooxyl) as a catalyst and 300 g of a Michael type adduct containing alkoxy propionic acid were placed and stirred at a temperature of 150° C. under normal pressure till they reacted. Four hours after the start of the reaction, the decomposition liquid was analyzed by gas chromatography. The results are shown in Table 1.

The Michael type adduct was composed of 46.5% by weight of n-butyl β-n-butoxy propionate acid (BPB), 20% by weight of n-butylβ-acryloxy propionate (APB), 2.5% by weight of phenothiazine, and 31% by weight of other high-boiling by-products.

COMPARATIVE EXAMPLE 1

A Michael type adduct was decomposed by a batch reaction by following the procedure of Example 1 while omitting the use of the 4H-TEMPO. The results were shown in Table 1. The composition of the Michael type adduct was identical with that used in Example 1.

COMPARATIVE EXAMPLE 2

A Michael type adduct was decomposed by cracking distillation by following the procedure of Example 3 while omitting the use of the 4H-TEMPO and changing the reflux ratio to 0.9. The results were shown in Table 1. The composition of the Michael type adduct was identical with that used in Example 1.

COMPARATIVE EXAMPLE 3

The decomposition of a Michael type adduct was carried out by following the procedure of Example 4 while omitting the use of the 4H-TEMPO. Four hours after the start of the reaction, the decomposition liquid was analyzed by gas chromatography. The results were shown in Table 1.

TABLE 1

| | Temperature (° C.) | 4H-TEMPO | Conversion DAA, (%) | Selectivity coefficient (%) |
|---|---|---|---|---|
| Example 1 | 140 | Used | 65 | 95 |
| Example 2 | 140 | Used | 70 | 96 |
| Example 3 | 140 | Used with NaOH | 75 | 98 |
| Example 4 | 140 | Used | 80 | 98 |
| Example 5 | 150 | Used | 60 | 80 |
| Comparative Example 1 | 140 | None | 30 | 65 |
| Comparative Example 2 | 140 | None | 50 | 70 |
| Comparative Example 3 | 150 | None | 32 | 55 |

It is noted from Table 1 that in Example 1 and Example 4, the conversions were higher and the selectivity coefficients for acrylic acid and/or acrylic ester were higher than in Comparative Example 1 or Comparative Example 2. Particularly, as compared with Example 5 and Comparative Example 3 which used a temperature of 150° C. for the treatment, the conversions and the selectivity coefficients were both lower when he 4H-TEMPO was absent. Comparison of Example 1 and Example 3 reveals that the addition of the alkali metal salt compound besides the N-oxyl compound improved the conversion and the selectivity coefficient.

EXAMPLE 6

Acrylic acid was produced by following the flow of production of acrylic acid illustrated in FIG. 1. For a start, an acrylic acid-containing gas obtained by supplying propylene (190) and a molecular oxygen-containing gas to the catalytic gas phase reactor (110) provided with an intermediate tube sheet partitioning the reactor into an upper and a lower chamber and subjecting the two compounds to catalytic gas phase oxidation was introduced into the acrylic acid absorption column (120) and brought into contact with water to collect acrylic acid in the aqueous solution. The acrylic acid-containing solution was found to contain acrolein as an impurity. This acrylic acid-containing solution was introduced into the acrolein dissipating column (130) to induce dissipation of acrolein and obtain an aqueous acrylic acid solution containing 30% by weight of water and 3.0% by weight of acetic acid.

This aqueous acrylic acid solution was introduced into the azeotropic dehydrating column (140) having an inside diameter of 105 mm and furnished with a stainless steel sieve tray formed of 50 steps spaced out 147 mm apart and provided in the column top part thereof with a distilling tube and a reflux supplying tube, in the central step (20$^{th}$ step) thereof with a raw material supplying tube and a polymerization inhibitor introducing tube, and in the column bottom part thereof with a bottoms extracting tube and a polymerization inhibitor introducing tube and toluene was used as an azeotropic solvent to effect distillation of an acrylic acid solution.

The operating conditions of the azeotropic dehydrating column (140) during the stationary operation were 50° C. in column top temperature, 105° C. in column bottom temperature, 170 hPa in column top pressure, 1.43 in reflux ratio (total number of moles of reflux liquid per unit time/total number of moles of distillate per unit time), and 12 tons/h in quantity of aqueous acrylic acid solution supplied. The water phase expelled by distillation through the top of the azeotropic dehydrating column (140) contained 7.5% by weight of acetic acid and 1.8% by weight of acrylic acid and the liquid extracted through the bottom of the column was composed of 97.5% by weight of acrylic acid, 0.03% by weight of acetic acid, 0.02% by weight of water, and 2.45% by weight of other components. The toluene content was less than the detectable limit (1 ppm).

The column bottom liquid was introduced into the rectifying column (150) furnished with a stainless steel sieve tray formed of 50 steps to obtain acrylic acid (200) as a finished product through the column top. The operating conditions of the rectifying column during the stationary operation were 35 hPa in column top operating pressure, 1.0 in reflux ratio, 92° C. in column bottom temperature, and 8.4 tons/h in quantity of supplied liquid. The bottom liquid of the rectifying column (150) was a liquid containing the Michael type adduct of acrylic acid dimer, for example and was composed of 30% by weight of acrylic acid dimer, 5% by weight of acrylic acid trimer, 60% by weight of acrylic acid, 5% by weight of maleic acid, and 5% by weight of stabilizer and high-boiling substances.

The bottom liquid containing the Michael type adduct was introduced at a rate of 0.8 ton/h to the intermediate step of the high-boiling separating column (160) furnished with a stainless steel sieve tray formed of 15 steps. The high-boiling separating column (160), with the bottom temperature thereof controlled to 90° C. by the thin-film distilling device (170), was operated under the conditions of 35 hPa in operating pressure and 1 in reflux ratio. Further, the bottoms of the thin-film distilling device (170) containing the Michael type adduct was introduced to the thermally decomposition tank (180). To the column (180), an N-oxyl compound (4-hydroxy-2,2,6,6-tetramethylpiperidinoxyl) was added in such a quantity as to account for 2% by weight relative to the waste liquid (300) containing the Michael type adduct extracted from the bottom of the decomposition tank (180) to decompose the Michael type adduct into acrylic acid with the interior of the decomposition tank kept at a temperature of 140° C. under normal pressure.

Part of the decomposition liquid was introduced again into the thin-film distilling device (170) to recover acrylic acid through the top of the high-boiling separating column (160) and into the liquid supplied to the azeotropic dehydrating column (140). Part of the decomposition liquid was withdrawn as waste liquid (300) out of the system. As a result, the conversion of the Michael type adduct was found to be 85% and the selectivity coefficient thereof to be 95%.

What is claimed is:

1. A method for the decomposition of a Michael type adduct of acrylic acid and/or acrylic ester, characterized by causing a Michael type adduct of acrylic acid and/or acrylic ester represented by the following formula [I] or [II] to react in the presence of an N-oxyl compound thereby decomposing said Michael type adduct into acrylic acid and/or acrylic ester and/or alcohol in the range of 130° C. to 180° C.

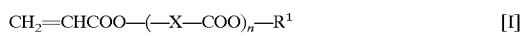

(wherein n denotes an integer of 1–5, $R^1$ denotes a hydrogen atom or an alkyl group, and —X— denotes —$CH_2CH_2$— or —$CH(CH_3)$—, providing that the plurality of —X— may be identical or not identical when n is not less than 2

(wherein m denotes an integer of 1–5, $R^2$ and $R^3$ independently denote a hydrogen atom or an alkyl group, and —X— denotes —$CH_2CH_2$— or —$CH(CH_3)$—, providing that the plurality of —X— may be identical or not identical when m is not less than 2.

2. A method according to claim 1, wherein the decomposition of a Michael type adduct of acrylic acid and/or acrylic ester and/or alcohol is performed in the presence of an alkali metal salt compound and/or an alkaline earth metal salt compound in addition to said N-oxyl compound.

3. A method for the production of acrylic acid and/or acrylic ester, characterized by comprising a step of recovering a Michael type adduct of acrylic acid and/or acrylic ester produced during the process for the production of acrylic acid or acrylic ester and a step of decomposing the recovered Michael type adduct of acrylic acid and/or acrylic ester by the method of decomposition set forth in claim 1 or claim 2.

4. A method according to claim 3, which further comprises, subsequently to the step of decomposing said Michael type adduct of acrylic acid and/or acrylic ester, a step of returning at least one compound selected from the group consisting of acrylic acid, acrylic ester, and alcohol obtained by decomposing said Michael type adduct of acrylic acid and/or acrylic ester to any one or more steps of producing acrylic acid and/or acrylic ester.

* * * * *